United States Patent [19]

Bedoukian

[11] Patent Number: 4,795,738

[45] Date of Patent: Jan. 3, 1989

[54] ARBOZOL CONTAINING PERFUME OR FRAGRANCE COMPOSITIONS

[75] Inventor: Robert H. Bedoukian, West Redding, Conn.

[73] Assignee: Bedoukian Research Inc., Danbury, Conn.

[21] Appl. No.: 116,027

[22] Filed: Nov. 3, 1987

[51] Int. Cl.[4] .................... A61K 7/46

[52] U.S. Cl. .................... 512/25; 512/2; 568/820

[58] Field of Search .................... 568/820; 512/2, 25

[56] References Cited

U.S. PATENT DOCUMENTS 4,107,094 8/1978 Light et al. .................... 512/25

FOREIGN PATENT DOCUMENTS 0126238 7/1985 Japan .................... 568/820

OTHER PUBLICATIONS

Bedoukian, R. H., Synthesis of Nonbornene Derivatives Possessing Woody Notes, 7th Int. Cong. Essential Oils, 1977 (Pap), vol. 7, 284–287 (1979).

*Primary Examiner*—Werren B. Lone
*Attorney, Agent, or Firm*—Parmelee, Bollinger & Bramblett

[57] ABSTRACT

Perfume or fragrance compositions containing arbozol to provide a very fresh, outdoor ocean air, woody and ozony odor with a slight cooling effect. The presence of arbozol in such compositions lifts woody and citrus notes, blends and soften harsh notes while imparting a freshness to such compositions and provides improved fixation properties and is excellent as a musk modifier on evaporation or dry-down and modifier of background notes.

14 Claims, No Drawings

ARBOZOL CONTAINING PERFUME OR FRAGRANCE COMPOSITIONS

FIELD OF THE INVENTION

The present invention relates to fragrance and perfume compositions or formulations containing arbozol as a fragrance and fragrance modifier and to a process for altering or modifying the properties, especially the dry-down properties of fragrance and perfume compositions by the addition of arbozo thereto.

BACKGROUND OF THE INVENTION

Many material are known which can provide fragrance characteristics to compositions or formulations in which it is desired to impart a fragrance. There is, however, an ongoing need for new fragrance materials to provide a unique fragrance. Moreover, many of the known fragrance compositions have undesirable harsh notes.

Additionally, in many fragrance compositions evaporation or dry-down leaves the compositions with undesirable odorous chemicals or chemical fragrances that overwhelm the main "bouquet" of the composition. For example, musk odorants are often employed in fragrance compositions as lifting agents but upon evaporation or dry-down the composition becomes overwhelmingly musky in fragrance. Accordingly, fragrance compositions have fixatives incorporated therein to slow down stages of evaporation or dry-down and to keep odors from evaporating or dissipating. However, most fixatives are themselves materials which provide a woody or musky odor and therefore may not be very suitable as fixatives for certain fragrance compositions. There is therefore a need for a new or improved fixative material that can be added to a perfume or fragrance composition and particularly a new or improved fixative that can act as a musk modifier on evaporation or dry-out so as to prevent the composition from becoming overwhelmingly musky in odor. There is also a need for a new or improved fixative that has a fresh outdoor, ocean air, ozony odor and has a slight cooling effect, that is, a fixative material that behaves like a lower boiling fragrance material yet which is a higher boiling material not subject to undue evaporation or dry-down.

SUMMARY OF THE INVENTION

It has been discovered that arbozol provide a fresh, ocean air, woody and ozony odor and a slight cooling effect to perfume or fragrance compositions in which it is incorporated. The presence of arbozol in said compositions lifts the woody and citrus notes, blends and soften harsh notes while imparting a freshness to such compositions and provides improved fixative properties. Moreover, arbozol is excellent as a musk modifier on evaporation or dry-down and a modifier of background notes. In such perfume or fragrance compositions arbozol unexpectedly behaves like a low-boiling fragrance material yet is a higher boiling material not subject to undue evaporation or dry-down.

Arbozol (CAS #73127-38-5), also known as 1-isopropenyl-5,6-dimethyl-5-norbornene-2-methanol or bicyclo[2.2.1]hept-5-ene-2-methanol-5,6-dimethyl-(1-methylethenyl), and its preparation has been reported in a paper entitled "Synthesis of Norbornene Derivatives Possessing Woody Notes" by Robert H. Bedoukian at the VII International Congress of Essential Oils in Kyoto, Japan in 1977. The preparation of arbozol as disclosed in said paper was solely for the purpose of confirming the structure of certain substituted norbornene esters which esters were disclosed as having woody, patchouli-vetivert like odors.

It has now been unexpectedly discovered that arbozol possesses the unique odor characteristic and fixative properties discussed hereinbefore while these characteristics and properties are not possessed by the substituted norbornene esters (methyl vetivate) from which arbozol is produced.

Arbozol is, for example, produced according to the following exemplary preparation.

ARBOZOL PREPARATION

About 800 grams of dehydrolinalool (I) is placed in a 2 liter flask equipped with stirrer, thermometer, water trap and reflux condenser, and heated to reflux for about 3 to 4 hours at about 185° C. to 195° C. until the conversion of dehydrolinalool to cyclodehydrolinalool (II) by cyclization is complete.

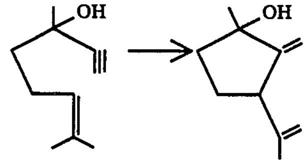

(I) (II)

To the cyclodehydrolinalool product, about 150 ml of xylene and about 60 ml of potassium tert-butoxide solution (15% in t-butanol) is added. The mixture is heated to 150° C. by distilling out the t-butanol for about four hours or until analysis of the reaction mixture indicates that the isomerization to 1,2-dimethyl-3-isopropenylcyclopent-2-en-1-ol (III) is complete. The reaction mixture is washed with about 300 ml of water.

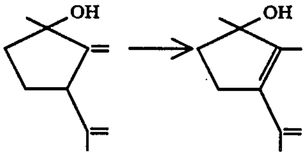

(II) (III)

To the organic phase, about 2 grams of citric acid is added. The reaction mixture is heated to about 50° C. with stirring. The heat is removed, and about 400 grams of methyl acrylate is added over about 3 to 5 hours. A mild exotherm is observed. At the end of the addition, the reaction mixture is heated to about 50°-60° C. for about two hours to produce crude 1-isopropenyl-2-carbomethoxy-5,6-dimethyl-5-norbornenes (IV).

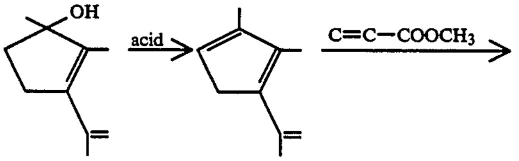

(III)

-continued

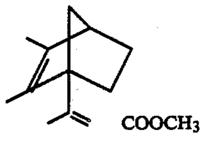

(IV)

This crude Diels-Alder product consisting primarily of 1-isopropenyl-2-carbomethoxy-5,6-dimethyl-5-norbornenes IV is dried by removing some of the xylene by distillation under vacuum until no more water is seen distilling with the xylene. The temperature is kept below 70° C. during the drying. About 400 ml toluene is added to the resulting mixture.

To a cooled 2 liter flask equipped with stirrer, and addition funnel there is charges about 830 grams of Vitride reducing agent (70% Sodium Bis(2-methoxyethoxy)-aluminum Hydride in toluene), and the above solution of crude ester (IV) is added at 0° C. under nitrogen.

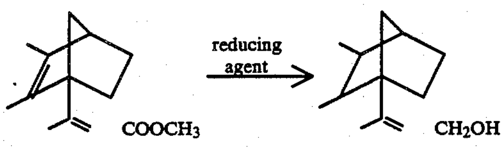

(IV) (V)

At the end of the reduction, excess Vitride is destroyed by the addition of acetone until no further exotherm is observed. The solution is washed once with 10% sodium hydroxide solution, and once with water.

Arbozol (V) is distilled through a packed column, and the fractions collecting at ca. 100° C. at 0.5 mm Hg are collected, yielding 250 grams of a clear, yellow viscous liquid. The product has a minimum purity of 90% by gas chromatography, a boiling polnt of 120° C. at 0.5 mm Hg, a refractive index of 1.51±0.01 at 25° C., a specific gravity of 0.98±0.01 at 20° C., a flash point of greater than 230° F. and is insoluble in water and soluble in alcohol.

Arbozol can be used to provide or contribute to a variety of perfumes or fragrances according to this invention. Thus, arbozol can be formulated into or used in conjunction with other fragrances as a component in perfumes or other similar fragrance compositions or formulations. Such perfume or fragrance compositions or formulations refer to a mixture of organic compounds, including for example, alcohols, aldehydes, ketones, nitriles, esters, natural essential oils and frequently hydrocarbons which are admixed so that the combined odors of the individual components produce a pleasant or desired fragrance. Such compositions usually contain: (a) the main note or the bouquet of the composition; (b) modifiers which round-off and accompany the main note; (c) fixatives which include odorous substances which lend a particular note to the composition throughout all stages of evaporation, and substances which retard evaporation; and (d) top-notes which are usually low-boiling fresh smelling materials.

In such compositions an individual component will contribute its particular olfactory characteristics, but the overall effect of the perfume composition will be the sum of the effect of each ingredient. Thus, arbozol, or mixtures thereof, with other fragrance components, can be used to alter the aroma characteristics of a composition, for example, by high-lighting or moderating the olfactory reaction contributed by another ingredient in the composition.

The amount of arbozol which will be effective in compositions depends on many factors, including the other ingredients, their amounts, and the effects which are desired. It has been found that fragrance compositions containing as little as 2% of arbozol, or even less, can be used to impart a scent to soaps, cosmetics, colognes, perfumes, and the other products. The amount employed can range up to 5 to 10% or higher and will depend on considerations of cost, nature of the end product, the effect desired on the finished product and the particular fragrance sought. Arbozol can be used alone or in a perfume composition as an olfactory component in detergents and soaps, space odorants and deodorants, perfumes, colognes, toilet waters, bath preparations such as bath oil and bath salts, hair preparations such as lacquers, brilliantines, pomades, and shampoos, cosmetic preparations such as creams, deodorant, hand lotions, and sun screens and powders such as talcs, dusting powders, face powder, and the like. When used a olfactory component of a perfumed article, as little as 0.2% of arbozol will suffice to impart a fresh, outdoor, ocean air, woody and ozony aroma. Generally, no more than 2% is required.

In addition, the perfume composition or fragrance composition can contain a vehicle or carrier for the arbozol alone or with other ingredients. The vehicle can be a liquid such as a non-toxic alcohol, glycol, or the like. The carrier can be an absorbent solid such as a gum or components for encapsulating the composition.

Moreover, the arbozol component of this invention is preferably employed in such perfume or fragrance compositions—as a fixative to impart improved fixative properties to the compositions and to function as a musk modifier on evaporation or dry-down of the compositions and to modify the background notes and particularly to lift woody and citrus notes. When used for such purposes in perfume and fragrance compositions, the arbozol will generally be present in an amount up to about 2% , generally in a range of from about 0.2 to about 2%.

Unless otherwise indicated, all parts, percentages, proportions and ratios set forth herein are by weight.

The following examples are given to illustrate the use of arbozol in accordance with this invention. However, it is understood that these examples are merely illustrative of embodiments of the invention and are not limited thereto.

EXAMPLE 1

Musk Modified Perfume

A perfume composition is formulated of the following components:

| Components | Parts |
|---|---|
| Arbozol | 20 |
| Amyl cinnamic aldehyde | 60 |
| Anethole USP | 5 |
| Anisyl alcohol | 10 |
| Benzyl acetate | 50 |
| Cestolidere | 15 |
| Cinnamic alcohol RIFM | 10 |
| Cresol p-methyl ether | 5 |
| Dihydromyrcenol | 10 |
| Dimetol | 20 |

-continued

| Components | Parts |
|---|---|
| Dipropylene glycol | 100 |
| Eugenol extra | 10 |
| p-Isopropyl cyclohexanol | 70 |
| Galaxolid 50 | 50 |
| Geraniol extra | 25 |
| Limonene D. redistilled | 15 |
| Linalool coeur | 40 |
| Lyyral | 40 |
| Nerone | 10 |
| Phenylacetaldehyde DMA | 85 |
| Phenylethyl alcohol | 120 |
| Rhodinol 70 | 130 |
| Styrallyl alcohol | 50 |
| Terpineol alpha | 30 |
| Tetrahydromuguol | 20 |
| Total | 1000 |

This formulation demonstrates the use of arbozol as a modifier of background notes which are the higher boiling components which remain after most of the other components have evaporated. In this formulation arbozol keeps the end note of the formulation from being simply a musk note by remaining behind with it to impart freshness and coolness. In contrast, a similar formulation without arbozol produces a formulation in which the end note is primarily a musk note.

EXAMPLES 2

Perfume Fixative Composition

A perfume composition is formulated of the following components:

| Components | Parts |
|---|---|
| Arbozol | 4.0 |
| Oranger crystals | 0.5 |
| Bergamot oil N/S | 18.2 |
| Galbanum coeur | 7.9 |
| Geranium oil Egypt | 0.5 |
| Hexenyl(cis-3-) salicylate | 0.9 |
| Jasmal | 0.5 |
| Lavandin abrialis oil | 3.7 |
| Lemon oil N/S | 11.1 |
| Limonene D. redistilled | 9.3 |
| Linalool pure | 4.6 |
| Linalyl acetate coeur | 9.3 |
| Methyl dihydrojasmonate | 0.9 |
| Orange oil Florida | 21.3 |
| Petitgrain oil SA | 3.7 |
| Rosmary oil Spanish | 1.9 |
| Terpinyl acetate | 1.9 |
| Total | 100.0 |

In this formulation arbozol significantly adds its unique fragrance contribution to the top and middle notes of the composition while also acting as a fixative to increase the lasting qualities of the fragrance of the composition.

Arbozol is unique in that it is a very lasting material with good fixative properties yet it also has a very perceptible effect in the top and middle notes of a blend.

Thus, it is very useful in fragrance compositions to lift woody and citrus notes. Furthermore, having its own freshness, it can lift or enhance a fragrance and do so without breaks or sudden changes in the fragrance as the composition dries down.

Other compositions can be formulated with arbozol employed as a fragrance, fragrance modifier and/or fixative in such compositions as soaps, detergents, colognes, toilet waters, bath oils, shampoos, deodorants, powders and the like.

I claim:

1. A perfume or fragrance composition containing a fragrance effective amount of arbozol.

2. A composition of claim 1 wherein arbozol is present in the composition in an amount up to about 10% by weight.

3. A composition of claim 1 wherein arbozol is present in the composition in an amount up to about 5% by weight.

4. A composition of claim 1 wherein arbozol is present in the composition in an amount up to about 2% by weight.

5. A method of modifying a background note in a perfume or fragrance composition on evaporation or dry-down comprising incorporating into the composition a background note modifying effective amount of arbozol.

6. A method of claim 5 wherein the arbozol is incorporated in the composltion in an amount of from about 0.2 to about 2% by weight.

7. A method of claim 5 wherein the arbozol is incorporated in the composition in an amount of about 2% by weight.

8. A method according to claim 5 for modifying the musk notes of a perfume or fragrance composition containing a musk fragrance comprising incorporating into the composition a musk modifying effective amount of arbozol.

9. A method of claim 8 wherein the arbozol is incorporated in the composition in an amount of from about 0.2 to about 2% by weight.

10. A method of claim 8 wherein the arbozol is incorporated in the composition in an amount of about 2% by weight.

11. A perfume or fragrance composition comprising main notes, modifiers and background notes and a fixative effective amount of arbozol.

12. A composition of claim 11 wherein a musk fragrance is present in the composition and arbozol is present in a musk modifying effective amount.

13. A composition according to claim 11 wherein the arbozol is present in an amount of from about 0.2 to about 2% by weight.

14. A composition according to claim 12 wherein the arbozol is present in an amount of from about 0.2 to about 2% by weight.

* * * * *